US008945590B2

(12) United States Patent
Fairman et al.

(10) Patent No.: US 8,945,590 B2
(45) Date of Patent: Feb. 3, 2015

(54) ENHANCEMENT OF AN IMMUNE RESPONSE BY ADMINISTRATION OF A CATIONIC LIPID-DNA COMPLEX (CLDC)

(75) Inventors: Jeffery Fairman, Mountain View, CA (US); Marla Lay Vaughn, Sunnyvale, CA (US)

(73) Assignee: Juvaris BioTherapeutics, Inc., Pleasanton, CA (US)

( * ) Notice: Subject to any disclaimer, the term of this patent is extended or adjusted under 35 U.S.C. 154(b) by 1268 days.

(21) Appl. No.: 12/411,377

(22) Filed: Mar. 25, 2009

(65) Prior Publication Data

US 2009/0263423 A1    Oct. 22, 2009

Related U.S. Application Data

(60) Provisional application No. 60/039,381, filed on Mar. 25, 2008.

(51) Int. Cl.
| | | |
|---|---|---|
| A61K 39/02 | (2006.01) | |
| A61K 39/12 | (2006.01) | |
| A61K 39/145 | (2006.01) | |
| A61K 39/116 | (2006.01) | |
| A61K 39/29 | (2006.01) | |
| A61K 39/295 | (2006.01) | |
| A61K 31/70 | (2006.01) | |
| A61K 39/085 | (2006.01) | |
| A61K 39/00 | (2006.01) | |

(52) U.S. Cl.
CPC ........... *A61K 39/0208* (2013.01); *A61K 39/085* (2013.01); *A61K 39/145* (2013.01); *A61K 39/292* (2013.01); *A61K 2039/5252* (2013.01); *A61K 2039/53* (2013.01); *A61K 2039/54* (2013.01); *A61K 2039/545* (2013.01); *A61K 2039/552* (2013.01); *A61K 2039/55505* (2013.01); *A61K 2039/55555* (2013.01); *A61K 2039/55561* (2013.01); *A61K 2039/55572* (2013.01); *A61K 2039/55577* (2013.01); *C12N 2730/10134* (2013.01); *C12N 2760/16134* (2013.01)
USPC .................. 424/278.1; 424/184.1; 424/209.1; 424/210.1; 424/227.1; 424/234.1

(58) Field of Classification Search
CPC ............ A61K 39/0208; A61K 39/145; A61K 39/292; A61K 39/085; A61K 2039/53; A61K 2039/54; A61K 2039/545; A61K 2039/55555; A61K 2039/55561; A61K 2039/55572; A61K 2039/55577; C12N 2760/16134; C12N 2730/10134
See application file for complete search history.

(56) References Cited

U.S. PATENT DOCUMENTS

| | | | |
|---|---|---|---|
| 4,877,612 A | * | 10/1989 | Berger et al. ............... 424/282.1 |
| 5,534,496 A | | 7/1996 | Lee et al. |
| 6,121,247 A | | 9/2000 | Huang et al. |
| 6,693,086 B1 | | 2/2004 | Dow et al. |
| 8,097,655 B2 | | 1/2012 | Davis |
| 2003/0022854 A1 | | 1/2003 | Dow et al. |
| 2003/0092663 A1 | | 5/2003 | Raz |
| 2004/0157791 A1 | | 8/2004 | Dow et al. |
| 2004/0247662 A1 | | 12/2004 | Dow et al. |
| 2005/0013812 A1 | | 1/2005 | Dow et al. |
| 2005/0181035 A1 | | 8/2005 | Dow et al. |
| 2006/0223769 A1 | | 10/2006 | Dow et al. |
| 2009/0162427 A1 | | 6/2009 | Dow et al. |
| 2009/0169612 A1 | | 7/2009 | Dow et al. |
| 2011/0002980 A1 | | 1/2011 | Dow et al. |
| 2012/0064151 A1 | | 3/2012 | Abraham |

FOREIGN PATENT DOCUMENTS

| | | |
|---|---|---|
| WO | WO 99/02132 A | 1/1999 |
| WO | WO 2009/105283 | 8/2009 |
| WO | WO 2009/120811 | 10/2009 |

OTHER PUBLICATIONS

Yokoyama, et al. DNA immunization: Effects of vehicle and route of administration on the induction of protective antiviral immunity. FEMS Immunology and Medical Microbiology 14 (1996) 22 1-230.*
Guy, et al. Design, characterization and preclinical efficacy of a cationic lipid adjuvant for influenza split vaccine. Vaccine 19 (2001) 1794-1805.*
Laird, et al. Forensic applications of the genomic matching technique: profiling the alpha block in the major histocompatibility complex. International Congress Series 1261 (2004) 580-582.*
Hada, M., et al., "Effect of separate injection of antigen and adjuvant on antibody production", Journal of Radiology and Physical Therapy, University of Kwanza, 99(1): 97-103 (1975).
Heijden, J., et al., "Separate application of adjuvant and antigen: the effect of a water-in-oil emulsion on the splenic plaque-forming cell response to sheep red blood cells in mice" Immunobiology, 171(1-2):143-154 (1986).
Hofland, H., et al., "In vivo gene transfer by intravenous administration of stable cationic lipid/DNA complex" Pharmaceutical Research, 14(6):742-749 (1997).
Oshop, G.L., et al., "In ovo delivery of DNA to the avian embryo" Vaccine 21(11-12):1275-1281 (2003).
Goodyear, A., et al., "Protection from pneumonic infection with *Burkholderia* species by inhalation immunotherapy" Infection and Immunity, American Association of Microbiology, 77(4):1579-1588, Apr. 2009.
Lay, M, et al., "Inverse relationship between innate and acquired immune responsiveness in mice initially dosed with catatonic lipid DNA complexes (JVRS-100)." FASEB Journal 2008; 22:1068.27.
Zhu, N, et al., "Systemic gene expression after intravenous DNA delivery into adult mice." Science 261:209-211, 1993.

(Continued)

*Primary Examiner* — Louise Humphrey
(74) *Attorney, Agent, or Firm* — Sughrue Mion, PLLC

(57) ABSTRACT

This invention relates to a method for vaccination which is effective for eliciting an enhanced antigen-specific immune response in a mammal, fish or bird. The method is particularly effective for protecting a mammal, fish or bird from a disease including cancer, a disease associated with allergic inflammation, or an infectious disease. Also disclosed are therapeutic compositions useful in such a method.

15 Claims, 12 Drawing Sheets

(56) References Cited

OTHER PUBLICATIONS

Figure 1:
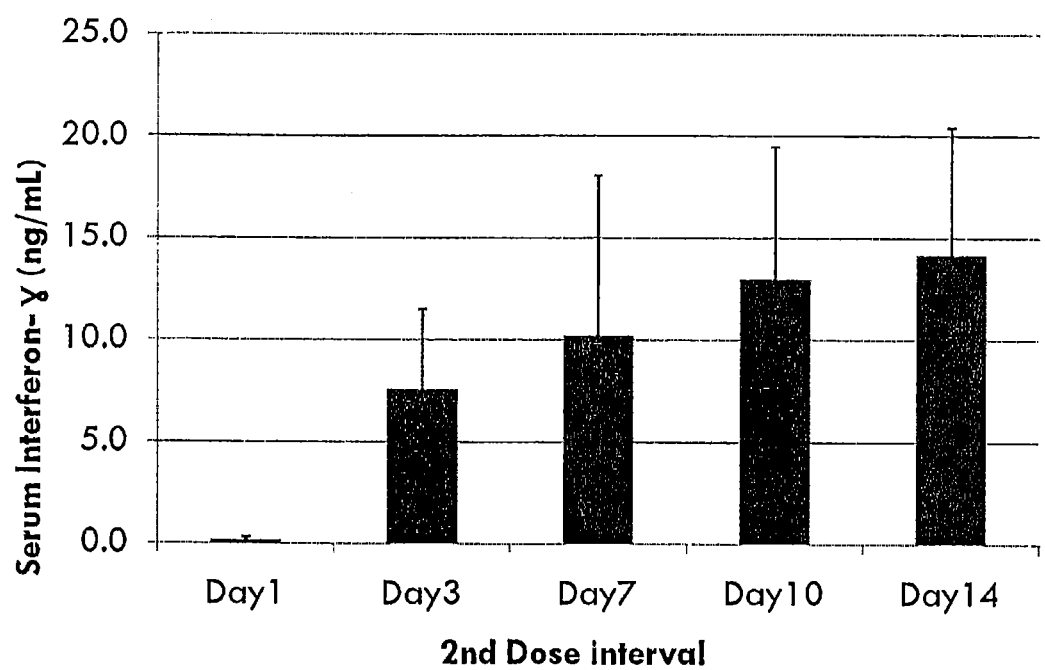

Gursel, I, et al., "Sterically stabilied catatonic liposomes improve the uptake and immunostimulatory activity of CpC oligonucleotides." J Immunol 167, 3324-3328, 2001.

Zaks, K, et al., "Efficient immunization and cross-priming by vaccine adjuvants containing TLR3 or TLR9 agonists complexed to cationic liposomes.", J Immunol. 176: 7335-7345, 2006.

Docke, WD, et al., "Monocyte deactivation in septic patients: restoration by IFN-gamma treatment." Nat Med. 3(6): 678-81, 1997.

Ziegler-Heitbrock HW, et al., "Tolerance to lipopolysaccharide in human blood monocytes." Immunobiology 193(2-4):217-23, 1995.

Lehner MD, et al., "Induction of cross-tolerance by lipopolysaccharide and highly purified lipoteichoic acid via different Toll-like receptors independent of paracrine mediators." J Immunol. 166(8): 5161-7, 2001.

Yeo, SJ, et al., "DNA induces self and cross-hyporesponsiveness of RAW264.7 cells in response to CpG DNA and lipopolysaccharide: alterations in IL-1 receptor-associated kinase expression." J Immunol. 170(2): 1052-61, 2003.

Troyer, R. et al., "Mucosal immunotherapy for protection from pneumonic infection with *Francisella tularensis*" Vaccine 27(33):4424-33, 2009.

Solodin et al., "A Novel Series of Amphiphilic Imidazolinium Compounds for in Vitro and in Vivo Gene Delivery." Biochemistry 34:13537-13544, 1995.
Liu et al., "Factors influencing the efficiency of cationic liposome-mediated intravenous gene delivery." Nature Biotech. 15:167-173, 1997.
Templeton, et al., "Improved DNA: liposome complexes for increased systemic delivery and gene expression." Nature Biotech. 15:647-652, 1997.
Van Hoecke C., et al., "Concomitant vaccination against hepatitis A any typhoid fever" J Travel Med 5:116-20, 1998.

* cited by examiner

ENHANCEMENT OF AN IMMUNE RESPONSE BY ADMINISTRATION OF A CATIONIC LIPID-DNA COMPLEX (CLDC)

CROSS REFERENCE TO RELATED APPLICATION(S)

This application claims the benefit of priority under 35 U.S.C. § 119(e) of U.S. Ser. No. 61/039,381, filed Mar. 25, 2008 the entire content of which is incorporated herein by reference.

GRANT INFORMATION

This invention was supported in part by NIH Grant No. 1R43AI060146-01A2, awarded by the National Institutes of Health. The United States government has certain rights in this invention.

BACKGROUND OF THE INVENTION

1. Field of the Invention

The invention relates generally to enhancing the immunogenicity and therefore the treatment of disease conditions with vaccines and more specifically to the utilization of a cationic liposome DNA complex (CLDC) to bolster the immunogenic capabilities of vaccines.

2. Background Information

In the early 1990's a gene delivery system was being developed that employed the use of liposomes complexed to plasmid DNA (coding) with the goal of eliciting expression of the delivered gene product in target tissues. Early on it was recognized that the injection of the complex of plasmid DNA and liposomes resulted in a profound activation of innate host immunity. This immune activation occurred whether or not the plasmid component was a coding vector or non-coding 'empty' vector. This effect was also significantly dependent upon formation of the complex of plasmid and cationic lipids, since neither entity alone had significant stimulatory properties except at exceedingly high in vivo doses. Since these early observations, it has become recognized that the stimulation of innate immunity triggered by cationic lipid-DNA complexes (CLDC) was due in part to a liposome-mediated potentiation of the inherent responsiveness of the mammal, fish or bird immune system to non-methylated CpG motifs within the bacterial DNA of the plasmids. Recently it has been recognized that CpG motifs function via interaction with the Toll-like receptor 9 (TLR-9) an interaction that requires internalization—an event that is facilitated significantly by the lipid component. Liposomes have been shown to enhance the immunostimulatory activity of CpG oligonucleotides (ODN) by 15-40 fold. The degree of immunostimulation by CLDC was so profound and predictable that it became known in the gene therapy field as the 'empty-vector' effect. This route-sensitive and dose-dependent effect has been recognized in multiple species and is characterized by almost immediate up-regulation of a broad-array of host soluble and cellular defenses. In addition to up-regulation of innate immunity, the immune stimulatory effect serves as a potent adjuvant for microbial and 'cancer' antigen-based vaccines.

Hyporesponsiveness to excessive innate immune stimulation has been studied extensively in vitro and documented in clinical treatment of sepsis patients. Characterization of the cells from these hyporesponsive patients indicated low inflammatory cytokine production in response to stimulus, reduced expression for HLA-DR, and generally a reduced capability for antigen presentation. This hyporesponsive state has also been demonstrated in vitro using human cells using lipopolysaccharide and lipoteichoic acid and recently in murine RAW264.7 cells using CpG oligonucleotides.

There is a continued need to provide better vaccines which can produce an immune response which is safe, antigen-specific and effective to prevent and/or treat diseases amenable to treatment by elicitation of an immune response, such as infectious disease, allergy and cancer.

The present invention assists the development of vaccines and vaccine strategies where a high level of protective titers are necessary following a single or a multiple vaccination or a combination of innate and adaptive immune response and protection is desired.

SUMMARY OF THE INVENTION

The present invention includes methods for eliciting an enhanced immune response to vaccination in mammals, fish or birds when a cationic lipid DNA complex (CLDC) is administered by an intravenous, intraperitoneal, inhalation or in ovo route concomitant with or followed by immunization with a vaccine antigen combined with or without an adjuvant. More particularly, the present invention relates to methods for eliciting a non-antigen specific immune response in a mammal, fish or bird using cationic liposome DNA complexes as the immune stimulant and vaccine adjuvant.

An embodiment of the present invention includes a method for eliciting an immune response in a mammal, fish or bird whereby a therapeutic dose of a cationic lipid DNA complex (CLDC) is administered via an intravenous, intraperitoneal, inhalation or in ovo route to the mammal, fish or bird. Either at the same time or after the CLDC is administered an adjuvanted or unadjuvanted vaccine; is administered via an intravenous, subcutaneous, intramuscular, intranasal or in ovo route. The resulting increase in immunogenicity may be the result of an enhanced antigen-specific immune response.

When the subject to be treated is a mammal the route of administration of the CLDC is via the IV, IP or inhalation route, with IV administration most preferred. The contemplated routes of administration of the adjuvanted or nonadjuvanted vaccine is via the IV, SC, IM or intranasal route, with the IM or SC routes most preferred.

When the subject to be treated is a bird or fish, the route of administration of the CLDC is via the IV, IP, inhalation or in ovo route, with IV or in ovo most preferred. The contemplated routes of administration of the adjuvanted or nonadjuvanted vaccine is via the IV, SC, IM, intranasal or in ovo route, with the IM, SC or in ovo routes most preferred.

When the vaccine is adjuvanted vaccine the vaccine may be adjuvanted with one or more of the following adjuvants: a cationic lipid DNA complex (CLDC), alum, Monophosphoryl Lipid A (MPL), QS21, or CpG oligonucleotide (CPG-ODN). The most preferred adjuvant is CLDC. In some contemplated embodiments, the adjuvant may include CLDC and at least one other adjuvant.

The administration protocols contemplated in the methods of the present invention require that an adjuvanted or non-adjuvanted vaccine is administered to the mammal, fish or bird concomitantly with or 0-7 days after the administration of the CLDC. Preferably, the vaccine is administered concomitantly with the CLDC, within hours afterwards, or within 1-3 days. Most preferably the vaccine is administered either concomitantly with or within 36 hours after CLDC administration.

Additional embodiments include methods wherein the vaccine is administered for the treatment of autoimmune diseases, cancer, allergic inflammation or infectious diseases. Some embodiments will include methods wherein the vaccine is administered for the prevention and treatment of primary lung cancers, pulmonary metastatic diseases, allergic asthma and viral diseases.

Additional embodiments include methods wherein the vaccine comprises an inactivated influenza A virus, an inactivated trivalent influenza vaccine, a split influenza vaccine, a glycosylated protein, a hepatitis B vaccine, or a lipopolysaccharide.

When the vaccine comprises an inactivated influenza A virus a preferred virus is HKx31. When the vaccine contains a trivalent influenza vaccine a preferred vaccine is the seasonally adjusted Fluzone® trivalent vaccine or an equivalent. When the vaccine comprises a glycosolated protein it is preferred that the glycosolated protein vaccine used to prevent or treat methacillin resistant *staphylococcus aureus* (MRSA). A preferred glycosolated protein is the Als3p-N protein. When the vaccine comprises a split influenza vaccine a preferred split influenza vaccine is the H5N1 split vaccine. When the vaccine comprises a Hepatitis B surface antigen a preferred vaccine is the ENGERIX-B or an equivalent. When the vaccine comprises lipopolysaccharide a glycosolated polysaccharide is preferred. Additionally, preferred polysaccharides include a *Francisella* polysaccharide and a *Francisella tularemia* LVS polysaccharide.

Another embodiment contemplated is a method of treating a mammal, fish or bird, with a disease condition by eliciting an enhanced antigen-specific immune response in said mammal, fish or bird by stimulating the immune response by administering a therapeutic dose of a cationic lipid DNA complex (CLDC); and administering a therapeutic dose of an adjuvanted or unadjuvanted vaccine. The administration of the CLDC is typically via an intravenous, intraperitoneal, inhalation or in ovo route; and the vaccine is typically administered via an intravenous, subcutaneous, intramuscular, intranasal or in ovo route, either concomitantly with said cationic lipid DNA complex (CLDC), or 0-7 days following said cationic lipid DNA complex (CLDC). Preferred embodiments administer the CLDC intravenously and the vaccine either via IM or SC for mammals, and include in ovo administration for both the CLDC and vaccine in fish or birds.

Disease conditions contemplated for treatment and/or prevention in the present invention may be selected from autoimmune diseases, cancer, allergic inflammation and infectious diseases. Preferred embodiments are directed towards the prevention and treatment of primary lung cancers, pulmonary metastatic diseases, allergic asthma and viral diseases.

Another embodiment discloses a method for eliciting an enhanced antigen-specific immune response in a mammal whereby a therapeutic dose of a cationic lipid DNA complex (CLDC) is administered intravenously and a therapeutic dose of an adjuvanted or unadjuvanted vaccine is administered intramuscularly or subcutaneously, concomitantly with or 0-7 days after said CLDC administration Another embodiment discloses a kit comprising the materials necessary to practice the disclosed methods of the present invention. The kit would include a first administrator comprising a therapeutic dose of a cationic lipid DNA complex (CLDC) for a mammal, fish or bird; a second administrator comprising a therapeutic dose of an adjuvanted or unadjuvanted vaccine for a mammal, fish or bird; and an instruction protocol for identifying the timing and routes of administration for each of the administrators. The preferred administrator is a syringe.

BRIEF DESCRIPTION OF THE DRAWINGS

The accompanying drawings, which are incorporated in and form a part of the specification, illustrate the preferred embodiment of the present invention, and together with the description serve to explain the principles of the invention. In the Drawings:

FIG. 1 graphically illustrates that there is a refractory period to multiple dosing with CLDC via intravenous administration that is resolved within 14 days.

FIG. 2 graphically illustrates that the refractory period to multiple dosing with CLDC via intravenous administration is dose dependent in magnitude.

FIG. 3 graphically illustrates that administration of an unadjuvanted vaccine containing an inactivated virus as the antigen (HKx31 influenza virus) within 1-7 days following IV administration of CLDC results in an enhanced anti-viral antibody response.

FIG. 4 graphically illustrates that administration of a CLDC adjuvanted purified vaccine (trivalent influenza vaccine—Fluzone®, Sanofi Pasteur) concomitantly or within 1-7 days following IV administration of CLDC results in an enhanced anti-viral antibody response.

FIG. 5 graphically illustrates that administration of an unadjuvanted vaccine containing an inactivated virus as the antigen (HKx31 influenza virus) one day following IV administration of CLDC results in an enhanced speed and intensity of the antibody response. The antibody response is indicated by geometric mean titer (GMT).

FIG. 6 graphically illustrates that an enhancement of vaccination occurs when the administration of a CLDC adjuvanted trivalent influenza vaccine occurs at the same time or after the IV administration of CLDC.

FIG. 7 graphically illustrates that IM administration of an unadjuvanted vaccine containing an inactivated virus as the antigen (HKx31 influenza virus) within 1-7 days following IV administration of CLDC results in an enhanced anti-viral antibody response.

FIG. 8*a* and FIG. 8*b* graphically illustrate that 8*a* subcutaneous (SC) pretreatment or 8*b* IM pretreatment with CLDC were ineffective for vaccine enhancement.

FIG. 9 graphically illustrates that IV pretreatment with CLDC enhances the vaccination response to methacillin resistant *Staphylococcus aureus* (MRSA).

FIG. 10 graphically illustrates that IV pretreatment with CLDC enhances the vaccination response to “Bird Flu” H5N1 influenza.

FIG. 11 graphically illustrates that IV pretreatment with CLDC enhances the vaccination response to a Hepatitis B surface antigen.

FIG. 12 graphically illustrates that IV pretreatment with CLDC enhances the vaccination response to *Francisella tularemia* LVS polysaccharide.

DETAILED DESCRIPTION OF THE INVENTION

The present invention generally relates to a novel immunization strategy and therapeutic compositions for eliciting an immune response in a mammal, fish or bird, and in particular, in a mammal, fish or bird that has a disease amenable to treatment by elicitation of an immune response. Diseases which are particularly amenable to treatment using the method of the present invention include autoimmune diseases, cancer, allergic inflammation and infectious disease. In one embodiment, the method and composition of the present invention are particularly useful for the prevention and treatment of primary lung cancers, pulmonary metastatic diseases, allergic asthma and viral diseases.

One embodiment of the present invention relates to a method of vaccination. The method contemplates the administration of cationic lipid DNA complex immune stimulant to a mammal, fish or bird via the intravenous route followed by administration of a cationic lipid DNA complex adjuvanted vaccine resulting in an enhanced immune response to the antigen included in the vaccine.

Examples of the present invention show that the intravenous (IV) administration of CLDC induces a short (7-10 day) refractory period to a innate immune activation to a second administration, with 50% of responsiveness restored after three days and 100% by 10-14 days. This refractory period was observed in interferon-gamma and interferon-gamma receptor knockout mice as well as mice pre-dosed with interferon-γ or depleted of NK cells or plasmacytoid dendritic cells. In contrast to reduced capacity for antigen presentation observed in sepsis patients, IV administration of CLDC simultaneously or up to seven days prior to vaccination with various antigens such as; HKx31 heat inactivated influenza virus, Fluzone® trivalent influenza vaccine, the glycosolated protein Als3p-N, H5N1 split vaccine, Hepatitis B surface antigen, and a *Francisella tularemia* LVS polysaccharide; adjuvanted with or without CLDC actually significantly enhanced both the humoral and cellular immune response. The enhancement of the adaptive response to vaccination was greatest at the timepoints at which the maximum refractory period was observed, suggesting an inverse relationship between these two observations. Therefore, despite the vaccine being administered when the interferon gamma levels were suppressed according to Example 1/FIG. 1 the vaccines tested were surprisingly more immunogenically responsive despite being administered during this refractory period. It was determined that the refractory period lasted for about 7-10 days after a systemic dose of CLDC was administered. The examples also clearly demonstrated that when a vaccine is administered concomitantly with or 0-7 days after the CLDC administration (the time period where interferon-gamma levels were most suppressed) the greatest boost of immunogenicity was found with multiple vaccines.

Additionally, the examples demonstrated that although an enhanced immunogenicity affect is found with some vaccines that are non-adjuvanted (see Example 3). Example 4 demonstrated that some non-adjuvanted vaccines may not have the same enhanced immunogenicity as the adjuvanted vaccine. It is generally preferable to use an adjuvanted vaccine, and most preferable to use a CLDC as the adjuvant.

Further additional examples demonstrated that the route of administration of the CLDC pretreatment or concomitant treatment is a necessary component. As further described in Example 8 and shown in FIGS. 8*a* and 8*b* neither subcutaneous nor intra-muscular administration of CLDC resulted in the enhanced immunogenic effects associated with the systemic administration. The results of experiment 8 are additionally beneficial for showing why a single SC or IM vaccine adjuvanted with CLDC does not result in an increased immunogenicity. Although, technically an SC or IM vaccine adjuvanted with CLDC is administered concomitantly with a CLDC (the adjuvant), Example 8 shows that an enhanced immunogenic response is not seen, therefore the enhanced immunogenicity of the present invention is not due to adjuvant effect alone. And it is preferable for the CLDC pretreatment or concomitant treatment to be administered systemically.

As used herein a non-adjuvanted vaccine means that neither the vaccine formulation or vaccine composition injected into the subject includes an any of the known adjuvants in concentrations sufficient to modify the effect of the vaccine. The terms non-adjuvanted and unadjuvanted are used interchangeably throughout the specification and are considered the same for the purposes of the present invention. Known adjuvants include but are not limited to: a cationic lipid DNA complex (CLDC), alum, Monophosphoryl Lipid A (MPL), QS21 (QS21 adjuvant is a nontoxic saponin derived from the soapbark tree *Quillaja saponaria*), or CpG oligonucleotide (CPG-ODN). The most preferred adjuvant is CLDC.

Embodiments of the present invention include administration protocols for administering CLDC to a subject concomitantly with or followed by an administration of a vaccine within 0-7 days after the CLDC administration which results in an enhanced immunogenic response in the subject.

An embodiment of the present invention includes a method for eliciting an immune response in a mammal, fish or bird whereby a therapeutic dose of a cationic lipid DNA complex (CLDC) is administered via an intravenous, intraperitoneal, inhalation or in ovo route to the mammal, fish or bird. Either at the same time or after the CLDC is administered, an adjuvanted or unadjuvanted vaccine; is administered via an intravenous, subcutaneous, intramuscular, intranasal or in ovo route. The resulting increase in immunogenicity may be the result of an enhanced antigen-specific immune response.

When the subject to be treated is a mammal the route of administration of the CLDC is via the IV, IP or inhalation route, with IV administration most preferred. The contemplated routes of administration of the adjuvanted or nonadjuvanted vaccine is via the IV, SC, IM or intranasal route, with the IM or SC routes most preferred.

When the subject to be treated is a bird or fish, the route of administration of the CLDC is via the IV, IP, inhalation or in ovo route, with IV or in ovo most preferred. The contemplated routes of administration of the adjuvanted or nonadjuvanted vaccine is via the IV, SC, IM, intranasal or in ovo route, with the IM, SC or in ovo routes most preferred.

When the vaccine is adjuvanted vaccine the vaccine may be adjuvanted with one or more of the following adjuvants: a cationic lipid DNA complex (CLDC), alum, Monophosphoryl Lipid A (MPL), QS21, or CpG oligonucleotide (CPG-ODN). The most preferred adjuvant is CLDC. In some contemplated embodiments, the adjuvant may include CLDC and at least one other adjuvant.

The administration protocols contemplated in the methods of the present invention require that an adjuvanted or non-adjuvanted vaccine is administered to the mammal, fish or bird concomitantly with or 0-7 days after the administration of the CLDC is administered. As used herein concomitant administration means that the CLDC is administered at the same time or contemporaneously with the adjuvanted or non-adjuvanted vaccine. Day 0 means that the CLDC is administered less that 24 hours before the adjuvanted or non-adjuvanted vaccine. Day 1 as used herein means that CLDC is administered between 24 hours and 48 hours before the adjuvanted or non-adjuvanted vaccine. Each of the following days up through day 7 are measured as 24 hour increments from the time the CLDC is administered.

Preferably, the vaccine is administered concomitantly with the CLDC, within hours afterwards, or within 1-3 days. Most preferably the vaccine is administered either concomitantly with or within 36 hours after CLDC administration.

Additional embodiments include methods wherein the vaccine is administered for the treatment of autoimmune diseases, cancer, allergic inflammation or infectious diseases. Some embodiments will include methods wherein the vaccine is administered for the prevention and treatment of primary lung cancers, pulmonary metastatic diseases, allergic asthma and viral diseases.

Additional embodiments include methods wherein the vaccine comprises an inactivated influenza A virus, an inactivated trivalent influenza vaccine, a split influenza vaccine, a glycosylated protein, a hepatitis B vaccine, or a lipopolysaccharide.

When the vaccine comprises an inactivated influenza A virus a preferred virus is HKx31. When the vaccine contains a trivalent influenza vaccine a preferred vaccine is the seasonally adjusted Fluzone® trivalent vaccine or an equivalent. When the vaccine comprises a glycosolated protein it is preferred that the glycosolated protein vaccine used to prevent or treat methacillin resistant *staphylococcus aureus* (MRSA). A preferred glycosolated protein is the Als3p-N protein. When the vaccine comprises a split influenza vaccine a preferred split influenza vaccine is the H5N1 split vaccine. When the vaccine comprises a Hepatitis B surface antigen a preferred vaccine is the ENGERIX-B or an equivalent. When the vaccine comprises lipopolysaccharide a glycosolated polysaccharide is preferred. Additionally, preferred polysaccharides include a *Francisella* polysaccharide and a *Francisella tularemia* LVS polysaccharide.

Another embodiment contemplated is a method of treating a mammal, fish or bird, with a disease condition by eliciting an enhanced antigen-specific immune response in said mammal, fish or bird by stimulating the immune response by administering a therapeutic dose of a cationic lipid DNA complex (CLDC); and administering a therapeutic dose of an adjuvanted or unadjuvanted vaccine. The administration of the CLDC is typically via an intravenous, intraperitoneal, inhalation or in ovo route; and the vaccine is typically administered via an intravenous, subcutaneous, intramuscular, intranasal or in ovo route, either concomitantly with said cationic lipid DNA complex (CLDC), or 0-7 days following said cationic lipid DNA complex (CLDC). Preferred embodiments administer the CLDC intravenously and the vaccine either via IM or SC for mammals, and include in ovo administration for both the CLDC and vaccine in fish or birds.

Disease conditions contemplated for treatment and/or prevention in the present invention may be selected from autoimmune diseases, cancer, allergic inflammation and infectious diseases. Preferred embodiments are directed towards the prevention and treatment of primary lung cancers, pulmonary metastatic diseases, allergic asthma and viral diseases.

Another embodiment discloses a method for eliciting an enhanced antigen-specific immune response in a mammal whereby a therapeutic dose of a cationic lipid DNA complex (CLDC) is administered intravenously and a therapeutic dose of an adjuvanted or unadjuvanted vaccine is administered intramuscularly or subcutaneously, concomitantly with or 0-7 days after said CLDC administration.

Elicitation of an immune response in a mammal, fish or bird can be an effective treatment for a wide variety of medical disorders, and in particular, for cancer, allergic inflammation and/or infectious disease. As used herein, the term "elicit" can be used interchangeably with the terms "activate", "stimulate", "generate" or "upregulate". According to the present invention, "eliciting an immune response" in a mammal, fish or bird refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a mammal, fish or bird from one which is harmful or ineffective to one which is beneficial or protective). For example, elicitation of a Th1-type response in a mammal, fish or bird that is undergoing a Th2-type response, or vice versa, may change the overall effect of the immune response from harmful to beneficial. Eliciting an immune response which alters the overall immune response in a mammal, fish or bird can be particularly effective in the treatment of allergic inflammation, mycobacterial infections, or parasitic infections. According to the present invention, a disease characterized by a Th2-type immune response (alternatively referred to as a Th2 immune response), can be characterized as a disease which is associated with the predominant activation of a subset of helper T lymphocytes known in the art as Th2-type T lymphocytes (or Th2 lymphocytes), as compared to the activation of Th1-type T lymphocytes (or Th1 lymphocytes). According to the present invention, Th2-type T lymphocytes can be characterized by their production of one or more cytokines, collectively known as Th2-type cytokines. As used herein, Th2-type cytokines include interleukin-4 (IL-4), interleukin-5 (IL-5), interleukin-6 (IL-6), interleukin-9 (IL-9), interleukin-10 (IL-10), interleukin-13 (IL-13) and interleukin-15 (IL-15). In contrast, Th1-type lymphocytes produce cytokines which include IL-12 and IFNγ. Alternatively, a Th2-type immune response can sometimes be characterized by the predominant production of antibody isotypes which include IgG1 (the approximate human equivalent of which is IgG4) and IgE, whereas a Th1-type immune response can sometimes be characterized by the production of an IgG2a or an IgG3 antibody isotype (the approximate human equivalent of which is IgG1, IgG2 or IgG3).

More specifically, a therapeutic composition as described herein, when administered to a mammal, fish or bird by the method of the present invention, preferably produces a result which can include alleviation of the disease, elimination of the disease, reduction of a tumor or lesion associated with the disease, elimination of a tumor or lesion associated with the disease, prevention of a secondary disease resulting from the occurrence of a primary disease (e.g., metastatic cancer resulting from a primary cancer), prevention of the disease, and stimulation of effector cell immunity against the disease.

Suitable liposomes for use with the present invention include any liposome. Additional information related to the liposomes and the making of use of the CLDC used in the present invention is described in U.S. Pat. No. 6,693,086 and is hereby incorporated by reference in its entirety.

Preferred liposomes of the present invention include those liposomes commonly used in, for example, gene delivery methods known to those of skill in the art. Preferred liposome delivery vehicles comprise multilamellar vesicle (MLV) lipids and extruded lipids. Methods for preparation of MLV's are well known in the art. According to the present invention, "extruded lipids" are lipids which are prepared similarly to MLV lipids, but which are subsequently extruded through filters of decreasing size, as described in Templeton et al., 1997, Nature Biotech., 15:647-652, which is incorporated herein by reference in its entirety. More preferred liposome delivery vehicles comprise liposomes having a polycationic lipid composition (i.e., cationic liposomes) and/or liposomes having a cholesterol backbone conjugated to polyethylene glycol. Preferred cationic liposome compositions include, but are not limited to DOTMA and cholesterol, DOTAP and cholesterol, DOTIM and cholesterol, and DDAB and cholesterol. A most preferred liposome composition for use as a delivery vehicle in the method of the present invention includes DOTIM and cholesterol.

In one embodiment of the present invention, the therapeutic dose of cationic lipid DNA complex (CLDC) may be replaced with any pattern recognition receptor ligand meant to elicit a systemic immune response.

Complexing a liposome with a nucleic acid molecule of the present invention can be achieved using methods standard in the art. According to the present invention a cationic lipid:

DNA complex is also referred to herein as a CLDC, and a cationic lipid:RNA complex is also referred to herein as CLRC. A suitable concentration of a nucleic acid molecule of the present invention to add to a liposome includes a concentration effective for delivering a sufficient amount of nucleic acid molecule into a mammal, fish or bird such that a systemic immune response is elicited. When the nucleic acid molecule encodes an immunogen or a cytokine, a suitable concentration of nucleic acid molecule to add to a liposome includes a concentration effective for delivering a sufficient amount of nucleic acid molecule into a cell such that the cell can produce sufficient immunogen and/or cytokine protein to regulate effector cell immunity in a desired manner. Preferably, from about 0.1 µg to about 10 µg of nucleic acid molecule of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes. In one embodiment, the ratio of nucleic acids to lipids (µg nucleic acid:nmol lipids) in a composition of the present invention is preferably at least about 1:1 nucleic acid:lipid by weight (i.e., 1 µg nucleic acid: 1 mmol lipid), and more preferably, at least about 1:5, and more preferably at least about 1:10, and even more preferably at least about 1:20. Ratios expressed herein are based on the amount of cationic lipid in the composition, and not on the total amount of lipid in the composition. In another embodiment, the ratio of nucleic acids to lipids in a composition of the present invention is preferably from about 1:1 to about 1:64 nucleic acid:lipid by weight; and more preferably, from about 1:5 to about 1:50 nucleic acid:lipid by weight; and even more preferably, from about 1:10 to about 1:40 nucleic acid:lipid by weight; and even more preferably, from about 1:15 to about 1:30 nucleic acid:lipid by weight. Another particularly preferred ratio of nucleic acid:lipid is from about 1:8 to 1:16, with 1:8 to 1:32 being more preferred. Typically, while non-systemic routes of nucleic acid administration (i.e., intramuscular, intratracheal, intradermal) would use a ratio of about 1:1 to about 1:3, systemic routes of administration according to the present invention can use much less nucleic acid as compared to lipid and achieve equivalent or better results than non-systemic routes. Moreover, compositions designed for gene therapy/gene replacement, even when administered by intravenous administration, typically use more nucleic acid (e.g., from 6:1 to 1:10, with 1:10 being the least amount of DNA used) as compared to the systemic immune activation composition and method of the present invention.

In another embodiment of the present invention, a therapeutic composition further comprises a pharmaceutically acceptable excipient. As used herein, a pharmaceutically acceptable excipient refers to any substance suitable for delivering a therapeutic composition useful in the method of the present invention to a suitable in vivo site. Preferred pharmaceutically acceptable excipients are capable of maintaining a nucleic acid molecule of the present invention in a form that, upon arrival of the nucleic acid molecule to a cell, the nucleic acid molecule is capable of entering the cell and being expressed by the cell if the nucleic acid molecule encodes a protein to be expressed. Suitable excipients of the present invention include excipients or formularies that transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with a preferred non-ionic buffer being 5% dextrose in water (DW5).

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Therapeutic compositions of the present invention can be sterilized by conventional methods and/or lyophilized.

According to the present invention, an effective administration protocol (i.e., administering a therapeutic composition in an effective manner) comprises suitable dose parameters and modes of administration that result in elicitation of an immune response in a mammal, fish or bird that has a disease, preferably so that the mammal, fish or bird is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of eliciting an immune response in a mammal, fish or bird with a disease when administered one or more times over a suitable time period. Doses can vary depending upon the disease being treated. In the treatment of cancer, a suitable single dose can be dependent upon whether the cancer being treated is a primary tumor or a metastatic form of cancer. Doses of a therapeutic composition of the present invention suitable for use with intravenous or intraperitoneal administration techniques can be used by one of skill in the art to determine appropriate single dose sizes for systemic administration based on the size of a mammal, fish or bird.

In a preferred embodiment, an appropriate single dose of a nucleic acid:liposome complex of the present invention is from about 0.1 µg to about 100 µg per kg body weight of the mammal, fish or bird to which the complex is being administered. In another embodiment, an appropriate single dose is from about 1 µg to about 10 µg per kg body weight. In another embodiment, an appropriate single dose of nucleic acid:lipid complex is at least about 0.1 µg of nucleic acid to the mammal, fish or bird, more preferably at least about 11 g of nucleic acid, even more preferably at least about 10 µg of nucleic acid, even more preferably at least about 50 µg of nucleic acid, and even more preferably at least about 100 µg of nucleic acid to the mammal, fish or bird.

Preferably, when nucleic acid:liposome complex of the present invention contains a nucleic acid molecule which is to be expressed in the mammal, fish or bird, an appropriate single dose of a nucleic acid:liposome complex of the present invention results in at least about 1 pg of protein expressed per mg of total tissue protein per µg of nucleic acid delivered. More preferably, an appropriate single dose of a nucleic acid: liposome complex of the present invention is a dose which results in at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered. When the route of delivery of a nucleic acid:lipid complex of the present invention is intraperitoneal, an appropriate single dose of a nucleic acid:liposome complex of the present invention is a dose which results in as low as 1 fg of protein expressed per mg of total tissue protein per µg of nucleic acid delivered, with the above amounts being more preferred.

A suitable single dose of a therapeutic composition of the present invention to elicit a systemic, non-antigen-specific immune response in a mammal, fish or bird is a sufficient amount of a nucleic acid molecule complexed to a liposome delivery vehicle, when administered intravenously or intraperitoneally, to elicit a cellular and/or humoral immune response in vivo in a mammal, fish or bird, as compared to a mammal, fish or bird which has not been administered with the therapeutic composition of the present invention (i.e., a control mammal, fish or bird). Preferred dosages of nucleic acid molecules to be included in a nucleic acid:lipid complex of the present invention have been discussed above.

A suitable single dose of a therapeutic composition to elicit an immune response against a tumor is a sufficient amount of a tumor antigen-encoding recombinant molecule, alone or in combination with a cytokine-encoding recombinant molecule, to reduce, and preferably eliminate, the tumor following lipofection of the recombinant molecules into cells of the tissue of the mammal, fish or bird that has cancer.

According to the present invention, a single dose of a therapeutic composition useful to elicit an immune response against an infectious disease and/or against a lesion associated with such a disease, comprising a pathogen-encoding recombinant molecule combined with liposomes, alone or in combination with a cytokine-encoding recombinant molecule with liposomes, is substantially similar to those doses used to treat a tumor (as described in detail above). Similarly, a single dose of a therapeutic composition useful to elicit an immune response against an allergen, comprising an allergen-encoding recombinant molecule combined with liposomes, alone or in combination with a cytokine-encoding recombinant molecule with liposomes, is substantially similar to those doses used to treat a tumor.

It will be obvious to one of skill in the art that the number of doses administered to a mammal, fish or bird is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to treat a given disease.

It is to be noted that the method of the present invention further differs from previously described gene therapy/gene replacement protocols, because the time between administration and boosting of the nucleic acid:lipid complex is significantly longer than the typical administration protocol for gene therapy/gene replacement. For example, elicitation of an immune response using the compositions and methods of the present invention typically includes an initial administration of the therapeutic composition, followed by booster immunizations at 3-4 weeks after the initial administration, optionally followed by subsequent booster immunizations every 3-4 weeks after the first booster, as needed to treat a disease according to the present invention. In contrast, gene therapy/gene replacement protocols typically require more frequent administration of a nucleic acid in order to obtain sufficient gene expression to generate or replace the desired gene function (e.g., weekly administrations).

A preferred number of doses of a therapeutic composition comprising a tumor antigen-encoding recombinant molecule, alone or in combination with a cytokine-encoding recombinant molecule, complexed with a liposome delivery vehicle in order to elicit an immune response against a metastatic cancer, is from about 2 to about 10 administrations patient, more preferably from about 3 to about 8 administrations per patient, and even more preferably from about 3 to about 7 administrations per patient. Preferably, such administrations are given once every 3-4 weeks, as described above, until signs of remission appear, and then once a month until the disease is gone.

According to the present invention, the number of doses of a therapeutic composition to elicit an immune response against an infectious disease and/or a lesion associated with such disease, comprising a pathogen antigen-encoding recombinant molecule, alone or in combination with a cytokine-encoding recombinant molecule, complexed with a liposome delivery vehicle, is substantially similar to those number of doses used to treat a tumor (as described in detail above).

A therapeutic composition is administered to a mammal, fish or bird in a fashion to elicit a systemic, non-antigen-specific immune response in a mammal, fish or bird, and when the nucleic acid molecule in the composition encodes an immunogen, to enable expression of the administered recombinant molecule of the present invention into an immunogenic protein (in the case of the tumor, pathogen antigen or allergen) or immunoregulatory protein (in the case of the cytokine) in the mammal, fish or bird to be treated for disease. According to the method of the present invention, a therapeutic composition is administered by intravenous or intraperitoneal injection, and preferably, intravenously. Intravenous injections can be performed using methods standard in the art. According to the method of the present invention, administration of the nucleic acid:lipid complexes can be at any site in the mammal, fish or bird wherein systemic administration (i.e., intravenous or intraperitoneal administration) is possible, particularly when the liposome delivery vehicle comprises cationic liposomes. Administration at any site in a mammal, fish or bird will elicit a potent immune response when either intravenous or intraperitoneal administration is used, and particularly, when intravenous administration is used. Suitable sites for administration include sites in which the target site for immune activation is not restricted to the first organ having a capillary bed proximal to the site of administration (i.e., compositions can be administered at an administration site that is distal to the target immunization site). In other words, for example, intravenous administration of a composition of the present invention which is used to treat a kidney tumor in a mammal, fish or bird can be administered intravenously at any site in the mammal, fish or bird and will still elicit a strong anti-tumor immune response and be efficacious at reducing or eliminating the tumor, even though the kidney is not the first organ having a capillary bed proximal to the site of administration. When a specific anti-tumor effect is desired (i.e., reduction or elimination of a tumor) and the route of administration is intravenous, the site of administration again can be at any site by which a composition can be administered intravenously, regardless of the location of the tumor relative to the site of administration. For intraperitoneal administration with regard to anti-tumor efficacy (but not immune activation/immunization), it is preferable to use this mode of administration when the tumor is in the peritoneal cavity, or when the tumor is a small tumor.

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rabbits, rats, sheep, cattle, horses and pigs, with humans and dogs being particularly preferred, and humans being most preferred. While a therapeutic composition of the present invention is effective to elicit an immune response against a disease in inbred species of mammals, the composition is particularly useful for eliciting an immune response in outbred species of mammals.

Additionally, for the present invention the methods and therapeutic compositions may be used to treat bird and fish, and most particularly poultry and or wild-birds which may be carriers of infectious diseases such as the avian flu.

As discussed above, a therapeutic composition of the present invention administered by the present method is useful for eliciting an immune response in a mammal, fish or bird having a variety of diseases, and particularly cancer, allergic inflammation and infectious diseases. A therapeutic composition of the present invention, when delivered intravenously or intraperitoneally, is advantageous for eliciting an immune response in a mammal, fish or bird that has cancer in that the composition overcomes the mechanisms by which cancer cells avoid immune elimination (i.e., by which cancer cells avoid the immune response effected by the mammal, fish or bird in response to the disease). Cancer cells can avoid immune elimination by, for example, being only slightly immunogenic, modulating cell surface antigens and inducing immune suppression. A suitable therapeutic composition for use in eliciting an immune response in a mammal, fish or bird that has cancer comprises a nucleic acid:lipid complex of the present invention, wherein the nucleic acid either is not operatively linked to a transcription control sequence, or more preferably, encodes a tumor antigen-encoding recombinant molecule operatively linked to a transcription control sequence, alone or in combination with a cytokine-encoding recombinant molecule (separately or together). A therapeutic composition of the present invention, elicits a systemic, non-specific immune response in the mammal, fish or bird and, upon entering targeted pulmonary or spleen and liver cells, leads to the production of tumor antigen (and, in particular embodiments, cytokine protein) that activate cytotoxic T cells, natural killer cells, T helper cells and macrophages. Such cellular activation overcomes the otherwise relative lack of immune response to cancer cells, leading to the destruction of such cells.

A therapeutic composition of the present invention which includes a nucleic acid molecule encoding a tumor antigen is useful for eliciting an immune response in a mammal, fish or bird that has cancer, including both tumors and metastatic forms of cancer. Treatment with the therapeutic composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy, and can be administered repeatedly. Moreover, the compositions administered by the method of the present invention typically target the vesicles of tumors, so that expression of a tumor antigen or cytokine within the tumor cell itself is not necessary to provide efficacy against the tumor. Indeed, a general advantage of the present invention is that delivery of the composition itself elicits a powerful immune response and expression of the nucleic acid molecule at least in the vicinity of the target site (at or adjacent to the site) provides effective immune activation and efficacy against the target.

A therapeutic composition of the present invention which includes a nucleic acid molecule encoding a tumor antigen is preferably used to elicit an immune response in a mammal, fish or bird that has a cancer which includes, but is not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. Particularly preferred cancers to treat with a therapeutic composition of the present invention include primary lung cancers and pulmonary metastatic cancers. A therapeutic composition of the present invention is useful for eliciting an immune response in a mammal, fish or bird to treat tumors that can form in such cancers, including malignant and benign tumors. Preferably, expression of the tumor antigen in a pulmonary tissue of a mammal, fish or bird that has cancer (i.e., by intravenous delivery) produces a result selected from the group of alleviation of the cancer, reduction of a tumor associated with the cancer, elimination of a tumor associated with the cancer, prevention of metastatic cancer, prevention of the cancer and stimulation of effector cell immunity against the cancer.

A therapeutic composition of the present invention which includes a nucleic acid molecule encoding an immunogen from an infectious disease pathogen is advantageous for eliciting an immune response in a mammal, fish or bird that has infectious diseases responsive to an immune response. An infectious disease responsive to an immune response is a disease caused by a pathogen in which the elicitation of an immune response against the pathogen can result in a prophylactic or therapeutic effect as previously described herein. Such a method provides a long term, targeted therapy for primary lesions (e.g., granulomas) resulting from the propagation of a pathogen. As used herein, the term "lesion" refers to a lesion formed by infection of a mammal, fish or bird with a pathogen. A therapeutic composition for use in the elicitation of an immune response in a mammal, fish or bird that has an infectious disease comprises a pathogen antigen-encoding recombinant molecule, alone or in combination with a cytokine-encoding recombinant molecule of the present invention, combined with a liposome delivery vehicle. Similar to the mechanism described above for the treatment of cancer, eliciting an immune response in a mammal, fish or bird that has an infectious disease with immunogens from the infectious disease pathogens with or without cytokines can result in increased T cell, natural killer cell, and macrophage cell activity that overcome the relative lack of immune response to a lesion formed by a pathogen. Preferably, expression of the immunogen in a tissue of a mammal, fish or bird that has an infectious disease produces a result which includes alleviation of the disease, regression of established lesions associated with the disease, alleviation of symptoms of the disease, immunization against the disease and stimulation of effector cell immunity against the disease.

A therapeutic composition of the present invention is particularly useful for eliciting an immune response in a mammal, fish or bird that has an infectious diseases caused by pathogens, including, but not limited to, bacteria (including intracellular bacteria which reside in host cells), viruses, parasites (including internal parasites), fungi (including pathogenic fungi) and endoparasites. Preferred infectious diseases to treat with a therapeutic composition of the present invention include chronic infectious diseases, and more preferably, pulmonary infectious diseases, such as tuberculosis. Particularly preferred infectious diseases to treat with a therapeutic composition of the present invention include human immunodeficiency virus (HIV), *Mycobacterium tuberculosis*, herpesvirus, papillomavirus and *Candida*.

In one embodiment, an infectious disease a therapeutic composition of the present invention is a viral disease, and preferably, is a viral disease caused by a virus which includes, human immunodeficiency virus, and feline immunodeficiency virus.

Preferred diseases associated with allergic inflammation which are preferable to treat using the method and composition of the present invention include, allergic airway diseases, allergic rhinitis, allergic conjunctivitis and food allergy.

A liposome delivery vehicle of the present invention can be modified to target a particular site in a mammal, fish or bird, thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms, such as targeting by addition of exogenous targeting molecules to a liposome (i.e., antibodies) are not a necessary component of the liposome delivery vehicle of the present invention, since effective immune activation at immunologically active organs is already provided by the composition and route of delivery of the present compositions without the aid of additional targeting mechanisms. Additionally, for efficacy, the present invention does not require that a protein encoded by a given nucleic acid molecule be expressed within the target cell (e.g., tumor cell, pathogen, etc.). The compositions and method of the present invention are efficacious when the proteins are expressed in the vicinity of (i.e., adjacent to) the target site, including when the proteins are expressed by non-target cells.

A preferred liposome delivery vehicle of the present invention is between about 100 and 500 nanometers (nm), more preferably between about 150 and 450 nm and even more preferably between about 200 and 400 nm in diameter.

Preparation of Cationic Lipid DNA Complexes (CLDC)

The cationic liposomes used in the following experiments (unless otherwise indicated) consisted of DOTAP (1,2 dioleoyl-3-trimethylammonium-propane) and cholesterol mixed in a 1:1 molar ratio, dried down in round bottom tubes, then rehydrated in 5% dextrose solution (D5W) by heating at 50.degree. C. for 6 hours, as described previously (Solodin et al., 1995, Biochemistry 34:13537-13544, incorporated herein by reference in its entirety). Other lipids (e.g., DOTMA) were prepared similarly for some experiments as indicated. This procedure results in the formation of liposomes that consists of multilamellar vesicles (MLV), which the present inventors have found give optimal transfection efficiency as compared to small unilamellar vesicles (SUV). The production of MLVs and related "extruded lipids" is also described in Liu et al., 1997, Nature Biotech. 15:167-173; and Templeton et al., 1997, Nature Biotech. 15:647-652; both of which are incorporated herein by reference in their entirety. Plasmid DNA (pCR3.1, Invitrogen) was purified from *E. coli* as described previously, using modified alkaline lysis and polyethylene glycol precipitation (Liu et al., 1997, supra). DNA for injection was resuspended in distilled water. Eukaryotic DNA (salmon testis and calf thymus) was purchased from Sigma Chemical Company. For many of the experiments reported here, the plasmid DNA did not contain a gene insert (unless otherwise noted), and is thus referred to as "non-coding" or "empty vector" DNA.

The cationic lipid DNA complexes (CLDC) used in the experiments below were prepared by gently adding DNA to a solution of lipid in 5% dextrose solution (D5W) at room temperature, then gently pipetting up and down several times to assure proper mixing. The DNA:lipid ratio was 1:8 (1.0 µg DNA to 8 nmol lipid). The CLDC were used within 30-60 minutes of preparation. To prepare small unilamellar vesicles (SUV) used in some experiments (as indicated), the CLDC that were formed using MLV liposomes as described above were subjected to sonication for 5 minutes, as described previously (Liu et al., 1997, supra).

Exemplary but not limited vaccines and disease states are featured below.

Trivalent Influenza Vaccine

Trivalent influenza vaccine which is defined as a synthetic vaccine consisting of three inactivated influenza viruses, two different influenza type A strains and one influenza type B strain. Trivalent influenza vaccine is formulated annually, based on influenza strains projected to be prevalent in the upcoming flu season. An example of a trivalent influenza vaccine is Fluzone®. Fluzone® is the commercial name of an influenza virus vaccine, distributed by sanofi pasteur, USA. It is a split-virus vaccine, which is produced by chemical disruption of the influenza virus. Therefore, it is incapable of causing influenza per se. As approved by the US Food and Drug Administration (FDA), Fluzone® is a preservative-free vaccine administered in a single dose by intramuscular injection. It is recommended for vaccination against type A and B influenza and is regularly optimised for various flu seasons.

Methicillin-Resistant *Staphylococcus aureus* (MRSA)

Methicillin-resistant *Staphylococcus aureus* (MRSA) is a bacterium responsible for difficult-to-treat infections in humans. It may also be referred to as multidrug-resistant *Staphylococcus aureus* or oxacillin-resistant *Staphylococcus aureus* (ORSA). MRSA is by definition a strain of *Staphylococcus aureus* that is resistant to a large group of antibiotics called the beta-lactams, which include the penicillins and the cephalosporins. New MRSA strains have rapidly spread in the United States to become the most common cause of cultured skin infections among individuals seeking medical care for these infections at emergency rooms in cities. These strains also commonly cause skin infections in athletes, jail and prison detainees, and soldiers.

Als3p-N

Als3p-N is a heavily glycosolated protein used as an antifungal vaccine and is derived from the recombinant N terminus of the Als3p protein it has been shown to protect mice against the bacterium *Staphylococcus aureus* and may be effective at treating strains of MRSA.

Influenza A Virus Subtype H5N1

Influenza A virus subtype H5N1, also known as "bird flu," A(H5N1) or simply H5N1, is a subtype of the Influenza A virus which can cause illness in humans and many other animal species. A bird-adapted strain of H5N1, called HPAI A(H5N1) for "highly pathogenic avian influenza virus of type A of subtype H5N1", is the causative agent of H5N1 flu, commonly known as "avian influenza" or "bird flu". It is enzootic in many bird populations, especially in Southeast Asia. It is epizootic (an epidemic in nonhumans) and panzootic (affecting animals of many species, especially over a wide area), killing tens of millions of birds and spurring the culling of hundreds of millions of others to stem its spread.

HPAI A(H5N1) is an avian disease. There is some evidence of limited human-to-human transmission of the virus. A risk factor for contracting the virus is handling of infected poultry, but transmission of the virus from infected birds to humans is inefficient. Still, around 60% of humans known to have been infected with the current Asian strain of HPAI A(H5N1) have died from it, and H5N1 may mutate or reassort into a strain capable of efficient human-to-human transmission.

Due to the high lethality and virulence of HPAI A(H5N1), its endemic presence, its increasingly large host reservoir, and its significant ongoing mutations, the H5N1 virus is the world's largest current pandemic threat, and billions of dollars are being spent researching H5N1 and preparing for a potential influenza pandemic.

Hepatitis B

Hepatitis B is a disease caused by hepatitis B virus which infects the liver of hominoidae, including humans, and causes an inflammation called hepatitis. Originally known as "serum hepatitis", the disease has caused epidemics in parts of Asia and Africa, and it is endemic in China. About a third of the world's population, more than 2 billion people, have been infected with the hepatitis B virus. This includes 350 million chronic carriers of the virus. Transmission of hepatitis B virus results from exposure to infectious blood or body fluids containing blood. The infection is preventable by vaccination.

ENGERIX-B

ENGERIX-B [Hepatitis B Vaccine (Recombinant)] is a noninfectious recombinant DNA hepatitis B vaccine developed and manufactured by GlaxoSmithKline Biologicals. It contains purified surface antigen of the virus obtained by culturing genetically engineered *Saccharomyces cerevisiae* cells, which carry the surface antigen gene of the hepatitis B virus. The surface antigen expressed in *Saccharomyces cerevisiae* cells is purified by several physicochemical steps and formulated as a suspension of the antigen adsorbed on aluminum hydroxide. ENGERIX-B is indicated for immunization against infection caused by all known subtypes of hepatitis B virus. As hepatitis D (caused by the delta virus) does not occur in the absence of hepatitis B infection, it can be expected that hepatitis D will also be prevented by ENGERIX-B vaccination.

*Francisella tularensis*

*Francisella tularensis* is a pathogenic species of gram-negative bacteria and the causative agent of tularemia or rabbit fever. *F. tularensis* is capable of infecting a number of small mammals such as voles, rabbits, and muskrats, as well as humans. Despite this, no case of tularemia has been shown to be initiated by human-to-human transmission. Rather, tularemia is caused by contact with infected animals or vectors such as ticks, mosquitoes, and deer flies. Infection with *F. tularensis* can occur via several routes. The most common occurs via skin contact, yielding an ulceroglandular form of the disease. Inhalation of bacteria—particularly biovar *tularensis*, leads to the potentially lethal pneumonic tularemia. While the pulmonary and ulceroglandular forms of tularemia are more common, other routes of inoculation have been described and include oropharyngeal infection due to consumption of contaminated food and conjunctival infection due to inoculation at the eye.

EXAMPLES

The examples herein are meant to exemplify the various aspects of carrying out the invention and are not intended to limit the invention in any way.

Example 1

A Refractory Period is Observed in Response to Multiple Dosing with CLDC Via Intravenous Administration that is Resolved within 10-14 Days Repeat dosing of CLDC has been shown to produce a refractory period to secondary dose. CD-1 (n=5) mice were intravenously administered 5 µg CLDC on day 0 followed by a second IV dose of 5 µg CLDC on the specified day. Serum was collected at 6 hours post second dose and immune activation was measured by ELISA for Interferon-γ. As can be seen in FIG. 1, at days 1, 3, and 7 the second dose of CLDC resulted in a lower systemic level of Interferon-γ. As can also be seen the lower systemic interferon-γ were not as pronounced at days 10 and 14. Thus it was determined that when IV doses of CLDC are administered in close within 1 to 7 days of the first CLDC dose the Interferon-γ response is suppressed, but this suppression was not as pronounced at days 10 and 14.

Example 2

Figure 2:
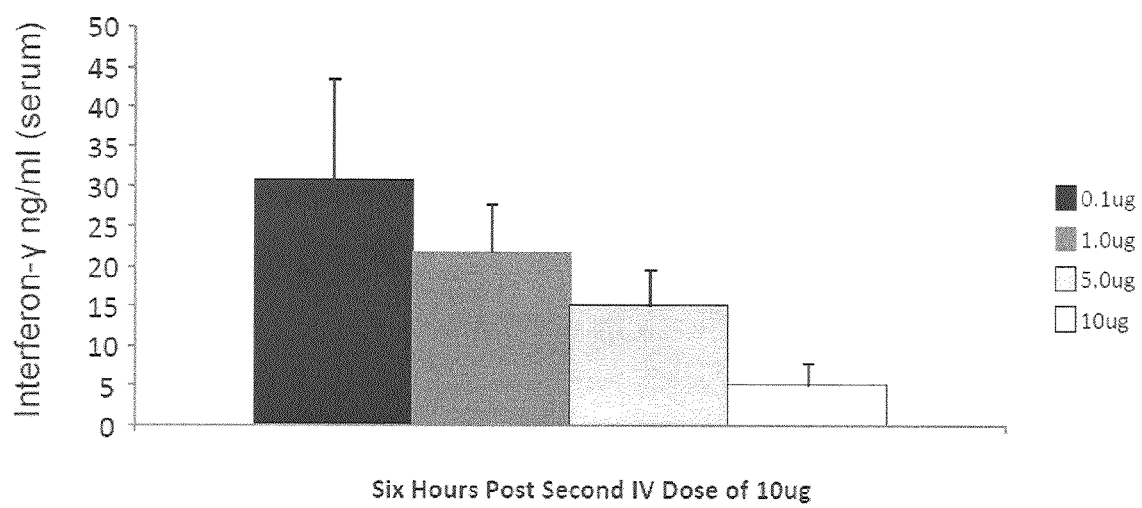

The Refractory Period to Multiple Dosing with CLDC Via Intravenous Administration is Dose Dependent in Magnitude Additional studies have shown that the magnitude of the initial refractory period is dose dependent (FIG. 2). CD-1 mice were intravenously administered one of four increasing doses of CLDC on day 0 followed by a second IV 10 µg dose on day 1. Innate immune activation was measured by ELISA assay for serum Interferon-γ 6 hours post second dose. These studies have shown that the refractory period due to CLDC is dose dependent in magnitude but not duration.

Example 3

Figure 3:
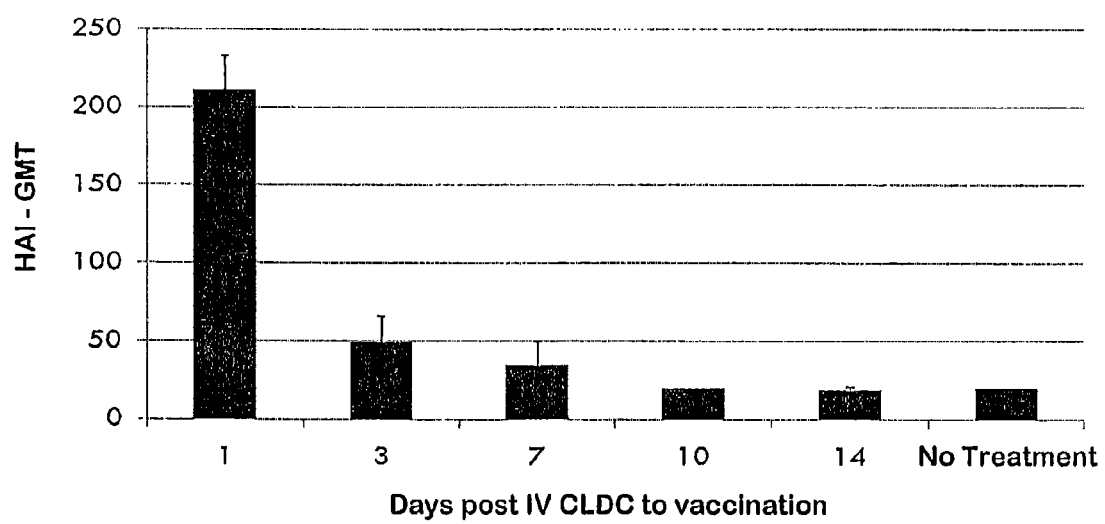

Administration of a Non-Adjuvanted Vaccine Containing an Inactivated Virus as the Antigen (HKx31 Influenza Virus) within 1-7 Days Following IV Administration of CLDC Results in an Enhanced Anti-Viral Antibody Response CD-1 mice were intravenously administered 5 µg CLDC on day 0 followed by a subcutaneous vaccination of 5 µg heat-inactivated HKx31 influenza virus on the specified day. Serum was collected at 21 days post vaccination and immunogenicity was measured by a hemagglutination inhibition titer (HAI). As shown in FIG. 3, despite the non-responsiveness to repeated administration to CLDC, administration of CLDC/HKx31 vaccine resulted in an increase in the anti-HKx31 vaccine response. Furthermore, the enhanced immunogenicity seen at 1, 3 and 7 days appears to be inversely correlated with the refractory period data discussed in example 1 and shown in FIG. 1. Therefore despite the vaccine being administered when the interferon gamma levels are suppressed according to FIG. 1 the vaccine is surprisingly immunogenically responsive despite this being administered during this refractory period.

Example 4

Trivalent Influenza Vaccination

Figure 4:
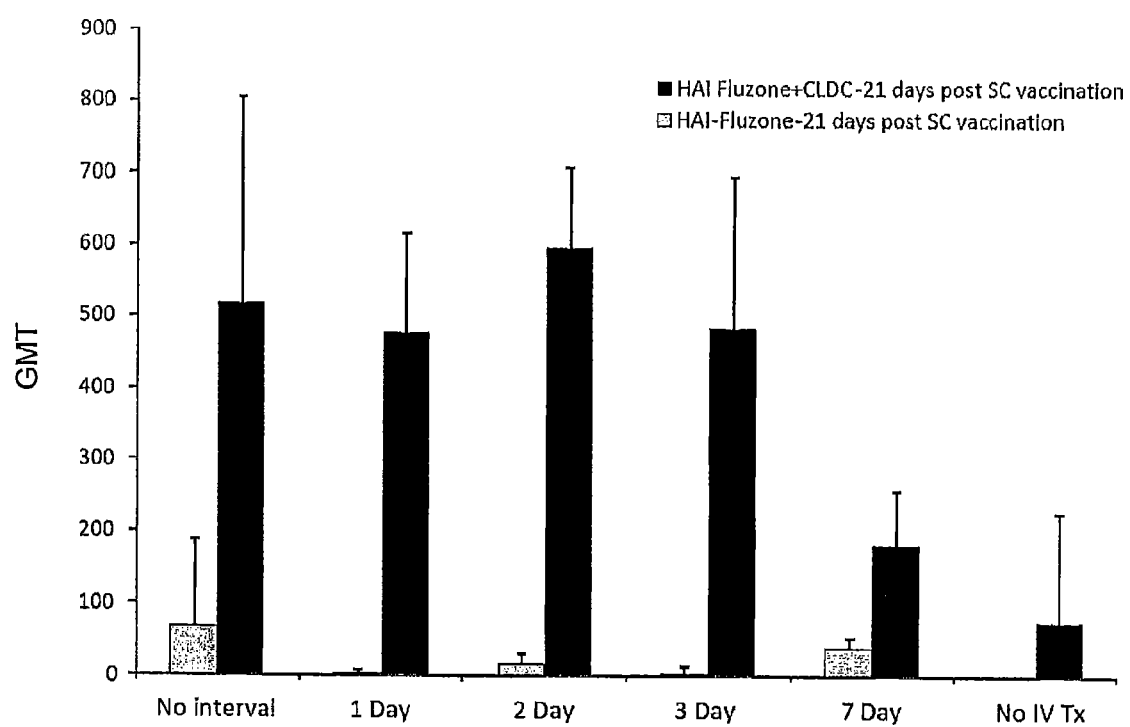

Administration of a Purified Vaccine (Trivalent Influenza Vaccine—Fluzone®, Sanofi Pasteur) Concomitantly or within 1-7 Days Following Iv Administration of CLDC Results in an Enhanced Anti-Viral Antibody Response One group of CD-1 (n=5) mice were intravenously administered 5 μg CLDC on day 0 followed by a subcutaneous vaccination of 5 μg Fluzone® (Sanofi Pasteur) adjuvanted with CLDC on the specified day. A second group of CD-1 mice were intravenously administered 5 μg CLDC on day 0 followed by a subcutaneous vaccination of 5 μg Fluzone® (Sanofi Pasteur) without additional adjuvant on the specified day. A third control group received no IV pretreatment of CLDC but were given a subcutaneous vaccination of adjuvanted or nonadjuvanted Fluzone®. Serum was collected at 21 days post vaccination and immunogenicity was measured by HAI using Fluzone as the antigen. As can be seen in FIG. 4, the enhanced anti-Fluzone® immune response was magnified approximately 8 fold higher than no IV treatment with CLDC. As can also be seen the enhancement of immunogenicity was not observed in mice administered CLDC via IV treatment followed by non-adjuvanted Fluzone®.

Example 5

Figure 5:
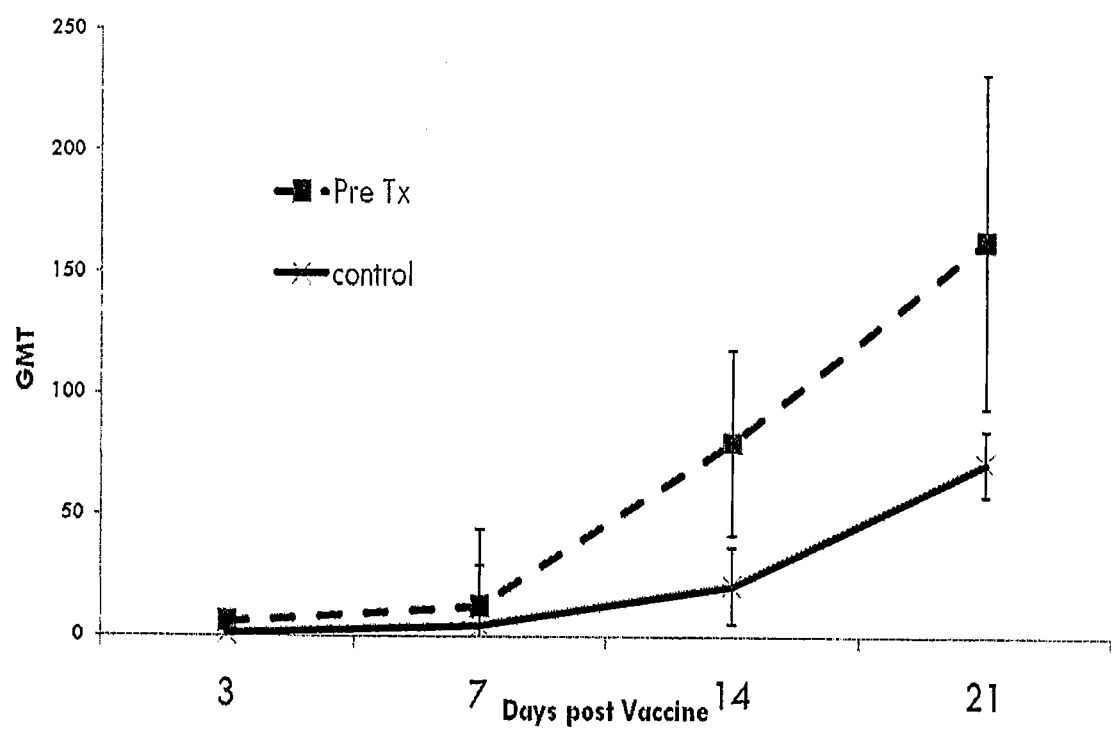

Systemic Pretreatment with CLDC Prior to Administering a Non-Adjuvanted Influenza A Vaccine Increases the Speed and Intensity of the Antibody Response CD-1 (n=5) mice were systemically administered 5 μg CLDC followed by an subcutaneous (SC) vaccination of a non-adjuvanted influenza A vaccine on the following day. 5 μg of heat inactivated A/HKx31 influenza virus was administered one day following the systemic administration of CLDC. Serum was collected on the specified day post vaccination and immunogenicity was measured by a hemagglutination inhibition titer (HAI). Serum was collected and tested at 3, 7, 14, and 21 days post vaccination. As shown in FIG. 5, an increased immunogenicity became pronounced sometime between day 7 and day 14 for the CLDC pretreatment animals. But increased immunogenicity did not occur in the control animals until about day 14 or after. Furthermore, the immunogenicity response for the controls was decreased at all time points as compared to the CLDC pretreatment animals.

Example 6

Enhancement of Vaccination is Optimized with IV Administration Occurring Concomitantly with or Prior to Vaccination CD-1 (n=5) mice were systemically administered 5 μg CLDC with a subcutaneous vaccination of 5 μg Fluzone+20 μg CLDC (25 μg trivalent influenza vaccine adjuvanted with CLDC) on the specified day. Mice were administered the trivalent influenza vaccine either 7, 3, or 1 day prior to the systemic administration of CLDC or concomitantly with or 2 days after the systemic administration of CLDC. Serum was collected at 21 days post vaccination and immunogenicity was measured by a hemagglutination inhibition titer (HAI).

Figure 6:
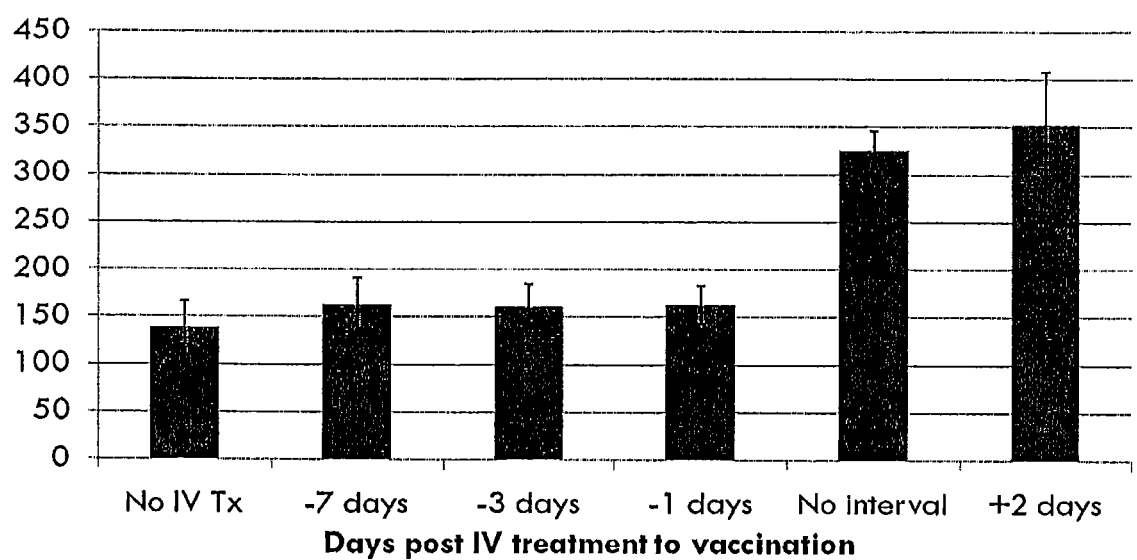

As shown in FIG. 6, administration of the adjuvanted trivalent influenza vaccine prior to the systemic administration of CLDC did not enhance immunogenicity. However, vaccination with the trivalent vaccine was enhanced when administered concomitantly or after systemic administration of CLDC.

Example 7

Figure 7:
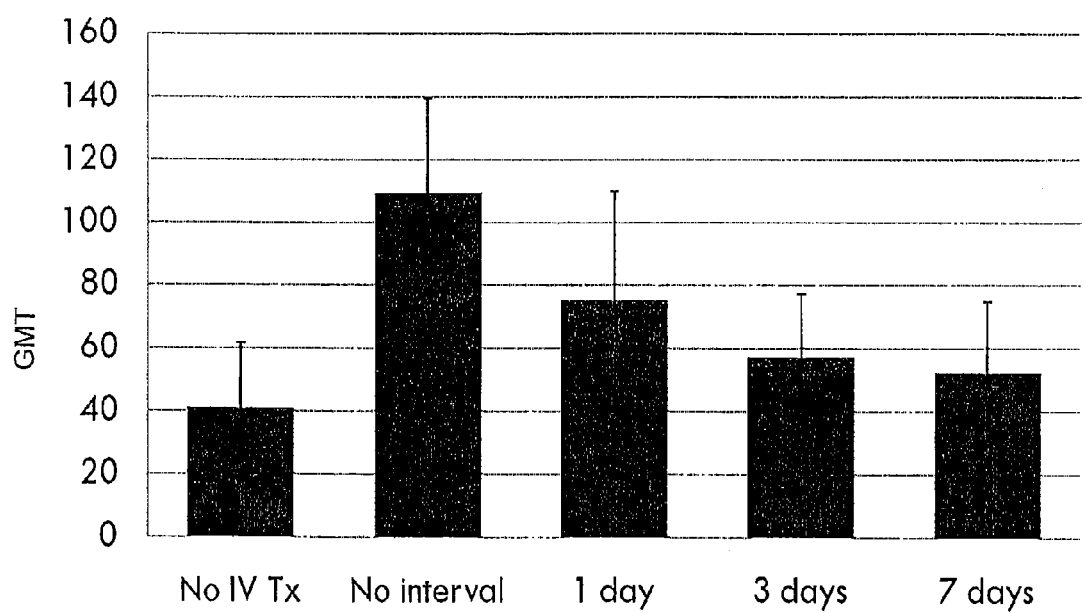

Enhancement of Vaccination can Occur with Multiple Routes of Vaccine Administration CD-1 (n=5) mice were systemically administered 5 μg CLDC followed by an intramuscular (IM) vaccination of a non-adjuvanted influenza A vaccine on the specified day. 5 μg of heat inactivated A/HKx31 influenza virus was administered at no interval/concomitantly, or on days 1, 3, or 7. Serum was collected at 21 days post vaccination and immunogenicity was measured by a hemagglutination inhibition titer (HAI). As shown in FIG. 7, IM administration of CLDC/HKx31 vaccine resulted in an increase in the anti-HKx31 vaccine response. Furthermore, the enhanced immunogenicity seen at each timepoint demonstrates that IM vaccination enhances immunogenicity and combined with the results of Example 3 shown in FIG. 3, demonstrate that vaccination is enhanced with either SC or IM administration of vaccine when administered concomitantly or after systemic IV administration of CLDC.

Example 8

CLDC Pretreatment Routes of Administration Studies

Figure 8A:
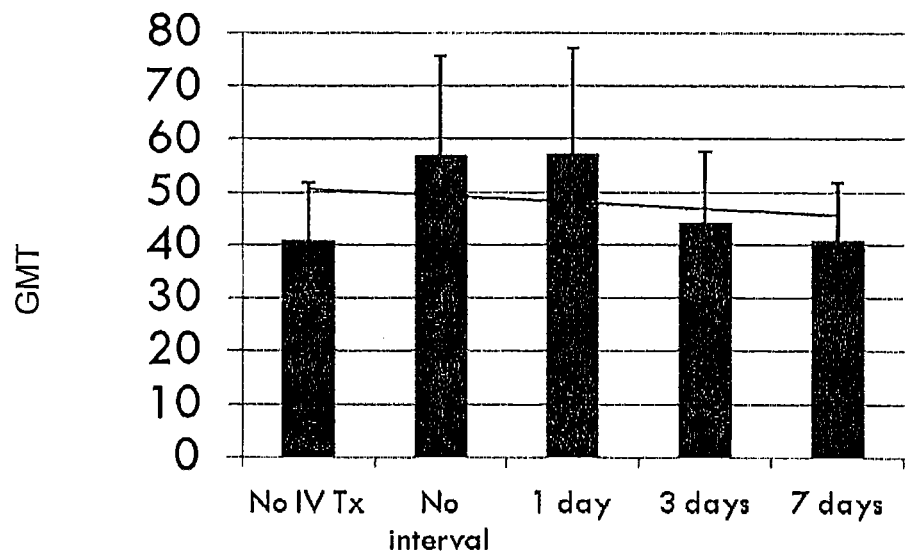
Figure 8B:
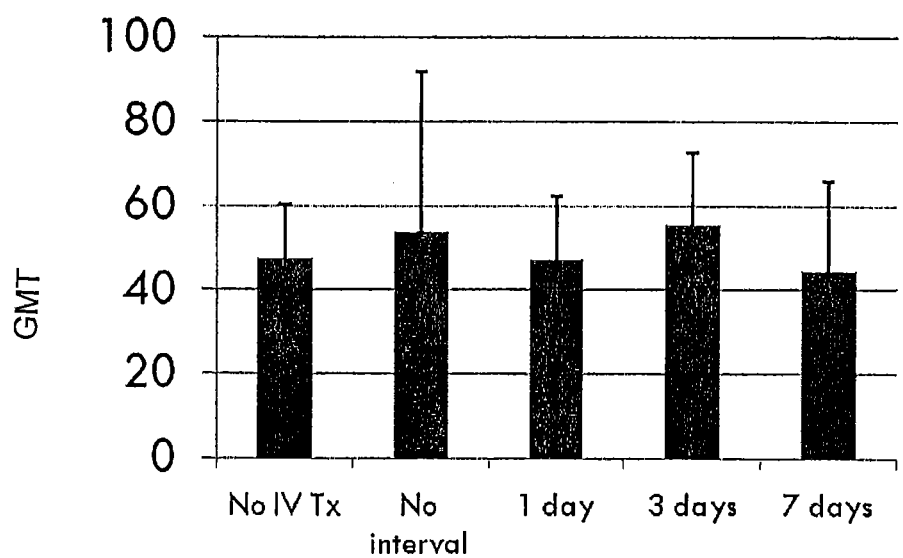

CD-1 (n=5) mice were pretreated with an intramuscular (IM) or subcutaneous (SC) administration of 20 μg CLDC followed by SC vaccination of a non-adjuvanted influenza A vaccine on the specified day. 5 μg of heat inactivated A/HKx31 influenza virus was administered at no interval/concomitantly, or on days 1, 3, or 7. Serum was collected at 21 days post vaccination and immunogenicity was measured by a hemagglutination inhibition titer (HAI). As shown in FIGS. 8a and 8b, neither SC or IM concomitant administration or pretreatment with CLDC enhanced immunogenicity. The following example demonstrates the route of administration of the CLDC is important in creating the enhanced immunogenic effect.

Example 9

Systemic Pretreatment with CLDC Enhances the Vaccination Response to Methacillin Resistant *Staphylococcus aureus* (MRSA)

Figure 9:
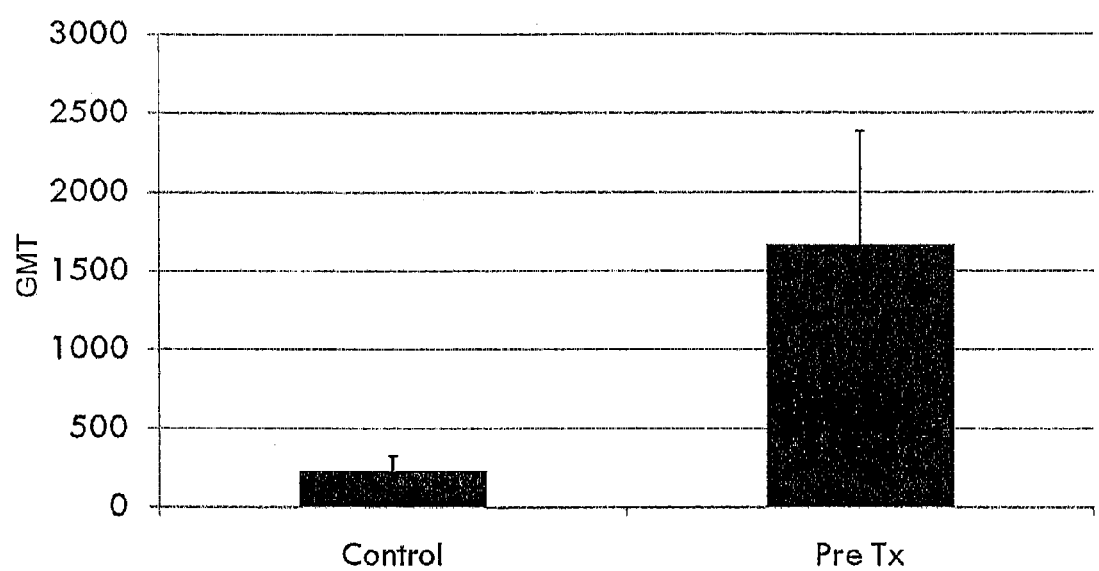

CD-1 (n=5) mice were intravenously administered 5 μg CLDC followed by a intramuscular vaccination of 5 μg rAls3p-N protein+20 μg CLDC on the following day. Control animals were intravenously an equal volume of 5% dextrose solution instead of CLDC then were vaccinated with an intramuscular vaccination of 5 μg rAls3p-N protein+20 μg CLDC. Serum was collected at 21 days post vaccination and immunogenicity was measured by ELISA antibody titer, an EC50 was calculated with Prism software. As can be seen in FIG. 9, the enhanced immune response as measured by the EC50 was magnified approximately 6-8 fold higher than the control no IV treatment with CLDC.

Example 10

Systemic Pretreatment with CLDC Enhances the Vaccination Response to "Bird Flu" H5N1 A

Figure 10:
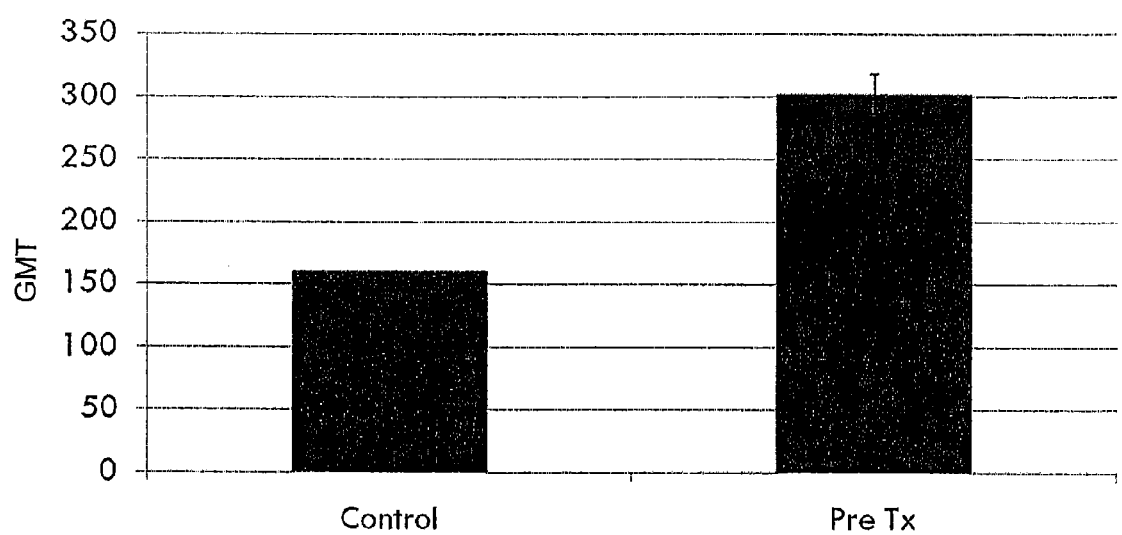

CD-1 (n=5) mice were intravenously administered 5 μg CLDC followed by a intramuscular vaccination of 1.5 μg H5N1+20% μg CLDC on the following day. Control animals were intravenously an equal volume of 5% dextrose solution instead of CLDC then were vaccinated with an intramuscular vaccination of 1.5% μg H5N1+20 μg CLDC. Serum was collected at 21 days post vaccination and immunogenicity was measured by a hemagglutination inhibition titer (HAI). As can be seen in FIG. 10, the mice showed a two fold improvement over controls and further demonstrates that split influenza vaccine (seasonal and pandemic) can be enhanced by systemic pretreatment with HLDC.

Example 11

Systemic Pretreatment with CLDC Enhances the Vaccination Response to Hepatitis B Surface Antigen

Figure 11:
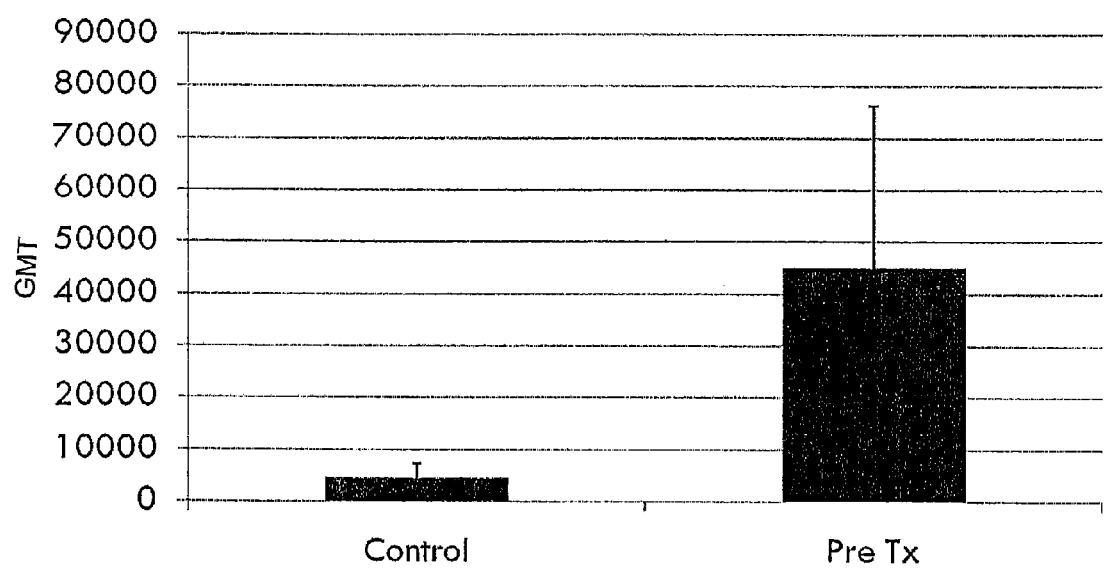

CD-1 (n=5) mice were intravenously administered 5 μg CLDC followed by a intramuscular vaccination of 2 μg Engerix+20 μg CLDC on the following day. Control animals were intravenously an equal volume of 5% dextrose solution instead of CLDC then were vaccinated with an intramuscular vaccination of 2 μg Engerix+20 μg CLDC. Serum was collected at 21 days post vaccination and immunogenicity was measured by ELISA antibody titer, an EC50 was calculated with Prism software. As can be seen in FIG. 11, the enhanced immune response as measured by the EC50 was magnified approximately 6-8 fold higher than the control no IV treatment with CLDC. The vaccine used was the Engerix-B hepatitis B surface antigen vaccine made by Merck, it contains an alum adjuvant. The above study demonstrates first, that systemic administration of CLDC can be used to enhance alum-adjuvanted vaccines; second, that CLDC administered with the vaccine can be used as an adjuvant with vaccines that are already adjuvanted; and third that systemic administration of CLDC can be used to enhance the immunogenicity of Hepatitis vaccines.

Example 12

**Systemic Pretreatment with CLDC Enhances the Vaccination Response to Methacillin Resistant *Francisella tularemia* LVS Polysaccharide**

Figure 12:
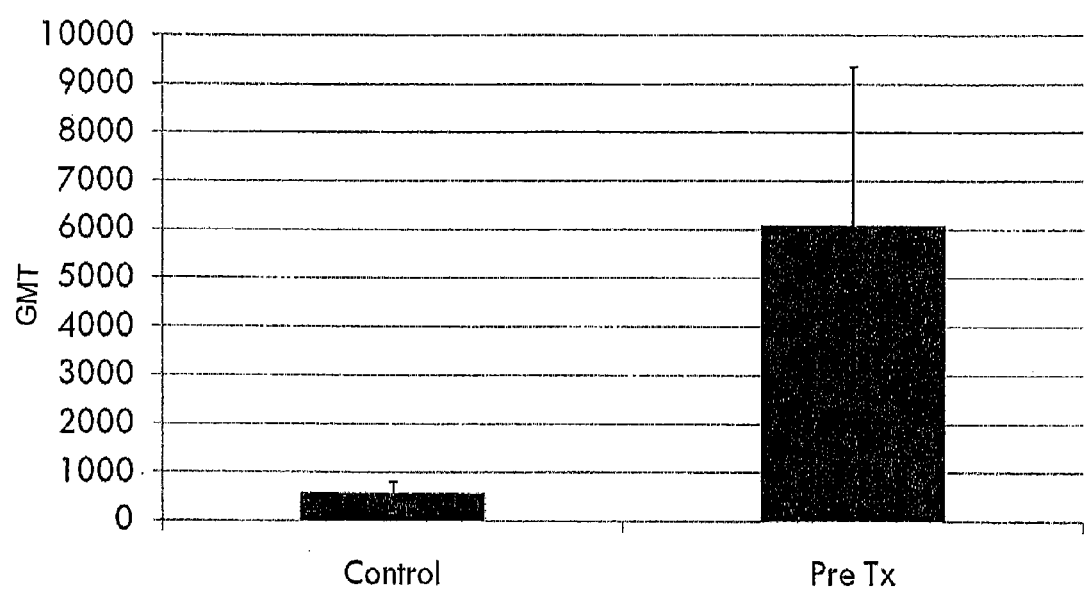

CD-1 (n=5) mice were intravenously administered 5 μg CLDC followed by a intramuscular vaccination of 5 μg FT-LVS+20 μg CLDC on the following day. Control animals were intravenously an equal volume of 5% dextrose solution instead of CLDC then were vaccinated with an intramuscular vaccination of 5 μg FT-LVS+20 μg CLDC. Serum was collected at 21 days post vaccination and immunogenicity was measured by ELISA antibody titer, an EC50 was calculated with Prism software. As can be seen in FIG. 12, the enhanced immune response as measured by the EC50 was magnified approximately 6-8 fold higher than the control no IV treatment with CLDC. The vaccine used was a *Francisella tularemia* LVS polysaccharide vaccine, adjuvanted with CLDC. The titer results demonstrates the general ability of systemic pretreatment of CLDC to enhance the immunogenicity of saccharide and lipopolysaccharide antigens, and more specifically to enhance the immunogenicity of a rabbit fever vaccine.

All references cited herein, including patents, patent applications, and publications, are hereby incorporated by reference in their entireties, whether previously specifically incorporated or not.

Although the invention has been described with reference to the above example, it will be understood that modifications and variations are encompassed within the spirit and scope of the invention. Accordingly, the invention is limited only by the following claims.

What is claimed is:

1. A method for eliciting an immune response in a mammal, fish or bird comprising:
   administering to a mammal, fish or bird a therapeutic dose of a cationic lipid DNA complex (CLDC);
   administering to a mammal, fish or bird a therapeutic dose of an adjuvanted or unadjuvanted vaccine comprising a protein, inactivated virus, split virion, or lipopolysaccharide;
   wherein said CLDC is administered via an intravenous, intraperitoneal, inhalation or in ovo route;
   wherein said vaccine is administered via an intravenous, subcutaneous, intramuscular, intranasal or in ovo route; and
   wherein said vaccine is administered concomitantly with or 0-7 days after said CLDC administration.

2. The method of claim 1 wherein the immune response is an enhanced antigen-specific immune response.

3. The method of claim 1 wherein said adjuvanted vaccine comprises one or more of the following adjuvants:
   a cationic lipid DNA complex (CLDC), alum, Monophosphoryl Lipid A (MPL), QS21, or CpG oligonucleotide (CPG-ODN).

4. The method of claim 3 wherein said adjuvant comprises CLDC alone.

5. The method of claim 1 wherein said vaccine comprises:
   an inactivated influenza A virus, an inactivated trivalent influenza vaccine, a split influenza vaccine, a glycosylated protein, a hepatitis B vaccine, or a lipopolysaccharide.

6. The method of claim 5 wherein said vaccine is adjuvanted.

7. The method of claim 5 wherein said vaccine is a split influenza vaccine.

8. The method of claim 7 wherein said split influenza vaccine is the H5N1 split vaccine.

9. The method of claim 1 wherein the method is for eliciting an immune response in a mammal comprising:
   administering a therapeutic CLDC intravenously to the mammal;
   administering a therapeutic dose of an adjuvanted or unadjuvanted vaccine intramuscularly or subcutaneously to the mammal;
   administering said vaccine concomitantly with or 0-7 days after said CLDC administration.

10. The method of claim 9 wherein said vaccine comprises:
    an inactivated influenza A virus, an inactivated trivalent influenza vaccine, a split influenza vaccine, a glycosylated protein, a hepatitis B vaccine, or a lipopolysaccharide.

11. The method of claim 9 wherein said adjuvanted vaccine comprises one or more of the following adjuvants:
    a cationic lipid DNA complex (CLDC), alum, Monophosphoryl Lipid A (MPL), QS21, or CpG oligonucleotide (CPG-ODN).

12. The method of claim 9 wherein said adjuvant comprises CLDC alone.

13. The method of claim 9 wherein the immune response is an enhanced antigen-specific immune response.

14. The method of claim 2 wherein the enhanced immune response is at least two-fold higher than a control with no CLDC administration.

15. The method of claim 14 wherein the enhanced immune response is approximately six to eight-fold higher than the control.

* * * * *